United States Patent [19]

Hutchins, IV

[11] 4,245,622
[45] Jan. 20, 1981

[54] INFLATABLE/DEFLATABLE DEVICE FOR A HEART-ASSIST PUMP

[76] Inventor: Thomas B. Hutchins, IV, 310 NW. Brynwood Ln., Portland, Oreg. 97220

[21] Appl. No.: 915,974

[22] Filed: Jun. 16, 1978

[51] Int. Cl.$^2$ .......................... A61F 1/24; A61M 1/03
[52] U.S. Cl. ...................................... 128/1 D; 3/1.7; 417/384
[58] Field of Search ............. 128/1 D, DIG. 3; 3/1.7; 417/384, 389, 394

[56] References Cited

U.S. PATENT DOCUMENTS

| | | | |
|---|---|---|---|
| 3,504,662 | 4/1970 | Jones | 128/1 D |
| 3,689,204 | 9/1972 | Prisk | 417/394 |
| 4,015,590 | 4/1977 | Normann | 128/1 D |
| 4,051,840 | 10/1977 | Kantrowitz et al. | 128/1 D |
| 4,116,589 | 9/1978 | Rishton | 128/1 D |

Primary Examiner—Dalton L. Truluck
Attorney, Agent, or Firm—Kolisch, Hartwell & Dickinson

[57] ABSTRACT

An inflatable/deflatable device for use in a body-implantable heart-assist pump. The device includes an inflatable/deflatable central portion, and a noninflatable, generally planar marginal portion joined thereto. In a preferred construction, the device is formed by the marginal joinder of a pair of flexible fluid-impervious sheets, wherein the central portion has opposite sides, and the marginal portion includes stretches distributed along these sides. The two flexible sheets may have different flexibilities, permitting the device to be inflated preferentially in a desired direction, and different curvatures, permitting the device to conform to adjoining surfaces in the heart-assist pump.

3 Claims, 8 Drawing Figures

INFLATABLE/DEFLATABLE DEVICE FOR A HEART-ASSIST PUMP

BACKGROUND AND SUMMARY

The present invention relates to inflatable/deflatable devices, and in particular to such a device for use in a body-implantable heart-assist pump.

A body-implantable heart-assit pump here denotes a pumping apparatus adapted to be connected across major aortae in the body to augment the pumping capacity of the heart. Such apparatus generally includes flexible inner and outer sleeves, the inner sleeve being connectable at its opposite ends to appropriate aortae. Positioned between the inner and outer sleeves is an inflatable/deflatable balloon which is connected by a fluid-exchange tube to a fluid-driving unit generally carried outside the body. As the balloon is alternately inflated and deflated under the influence of a recurrent, cyclic supply and exhaust of fluid from the driving unit, the inner sleeve is alternately closed and opened, and blood is, accordingly, pumped through the inner sleeve.

Heretofore, inflatable/deflatable balloons designed for the above-described use have had a generally stocking-type construction, providing an elongate, cylindrical structure closed at one end and communicating at the other end with a fluid-exchange tube. Such prior art balloons, when inflated, have a generally circular cross section, and as a result, may migrate undesirably during operation. Such migration, in the extreme, can seriously impair the efficiency of a pumping operation.

It is, therefore, a principal object of the present invention to provide for use in a heart-assist pump, an inflatable/deflatable device having a construction which substantially prevents the above-discussed migrating tendency.

Yet another object of the invention is to provide such a device which can be distended preferentially in a desired direction.

Another object of the invention is to provide such a device which, when deflated, has a generally curved cross-sectional shape conforming to adjoining wall portions of the sleeves forming a pump of the type mentioned.

A preferred embodiment of the invention includes a balloon device having an inflatable/deflatable central portion, and a noninflatable, generally planar marginal portion joined thereto. The central and marginal portions are formed through the marginal joinder of a pair of flexible fluid-impervious sheets, with the marginal portion including stretches distributed along opposite sides of the central portion. The two sheets have different flexibilities, such that inflation occurs preferentially in the direction of the sheet having the greater flexibility. Further, the two sheets are joined and dimensioned in such a way to produce a generally curved transverse cross section for the device when the same is in a relaxed state.

These and other objects and features of the present invention will now be more fully described with reference to the detailed description of the following embodiments of the invention, and the accompanying drawings.

DRAWINGS

DETAILED DESCRIPTION OF THE INVENTION

Figure 1:
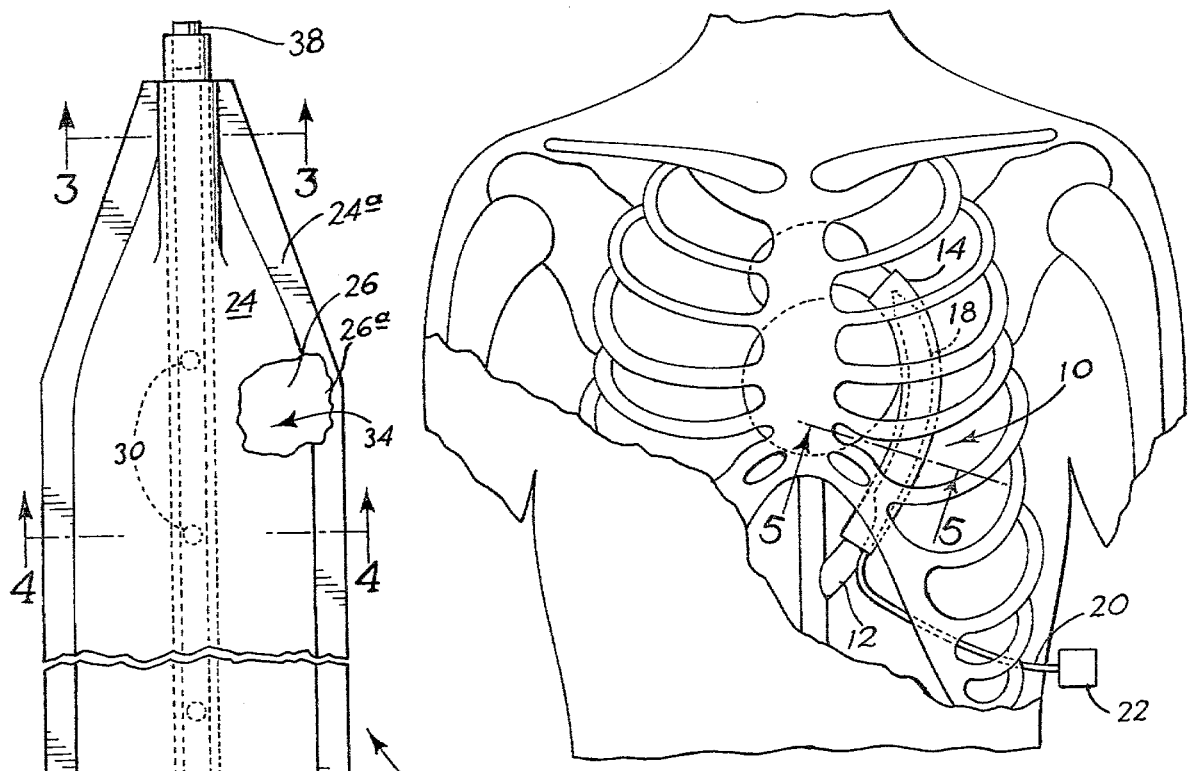
FIG. 1 illustrates a heart-assist pump employing the device of the present invention, with the pump shown in relation to a human trunk.
Figures 5, 6:
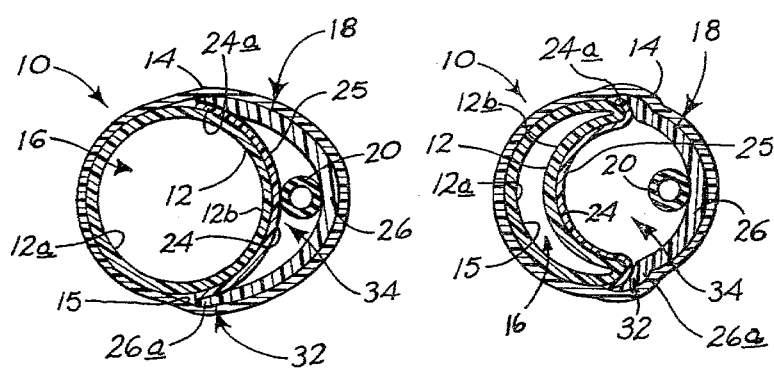
FIG. 5 is a sectional view taken generally along line 5—5 in FIG. 1, showing a heart-assist pump employing the device of FIGS. 2-4, inclusive, with the device in a deflated and relaxed condition.
FIG. 6 is a view similar to FIG. 5 but showing the device in an inflated condition.

Referring first to FIG. 1, there is shown generally at 10 a heart-assist pump employing an inflatable/deflatable device, such as that proposed by the present invention. Pump 10 includes an elongate envelope, or outer sleeve 14 having an inner wall 15 which is generally rounded in cross section, as can be seen in FIGS. 5 and 6. An inner sleeve 12, also referred to herein as a first elongate pumping member, includes, with reference to FIGS. 5 and 6, an outer wall portion 12a in contact with wall 15 and an inner wall portion 12b which is movable between a generally convex configuration, seen in FIG. 5, and a generally concave configuration, seen in FIG. 6, thus to increase and decrease, respectively, the volume of the sleeve's lumen, or chamber 16.

Positioned between sleeves 12, 14, in a manner to be explained, is an inflatable/deflatable device 18 (see FIG. 2 along with FIG. 1) constructed in accordance with the present invention. Device 18 is connected by a fluid-exchange tube 20 to a fluid-driving unit 22 generally carried outside the body. As device 18 is alternately inflated and deflated under the influence of a cyclic supply and exhaust of air from unit 22, chamber 16 is alternately closed and opened, as will be described. Device 18 is also referred to herebelow as a second elongate pumping member, and tube 20 is referred to herebelow as conduit means for carrying external fluid to and from the device.

Figure 2:
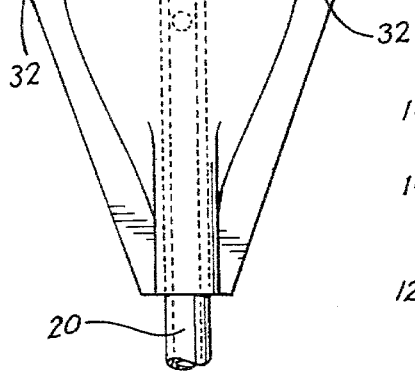
FIG. 2 is an enlarged, foreshortened plan view of a device constructed according to a preferred embodiment of the invention, and removed from other structure.
Figure 3:
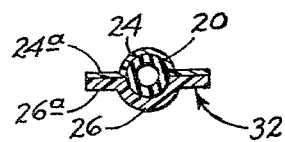
FIG. 3 is a sectional view of the device of FIG. 2 taken generally along line 3—3 in FIG. 2.
Figure 4:
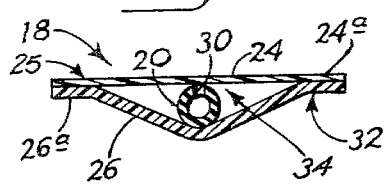
FIG. 4 is a sectional view of the device of FIG. 2 taken generally along line 4—4 in FIG. 2.

With reference to FIGS. 2-4, device 18 is formed from a pair of elongate flexible, fluid-impervious sheets 24, 26, each preferably having the general perimetral shape shown in FIG. 2. Sheet 24, which is also referred to herebelow as an inner sheet, includes opposed elongate side margins, such as margin 24a seen in FIGS. 4-6. The central region of sheet 24, between the side margins thereof, and indicated at 25 in FIGS. 4-6, is also referred to herein as the inner wall portion of sheet 24. Sheet 26 which is also referred to herein as an outer sheet, includes opposed elongate side margins, such as margin 26a seen in FIGS. 4-6. The associated coextending side margins of sheets 24, 26 are sealed together to form a pair of opposed, fluid-impermeable, noninflatable planar margins 32, and an inflatable/deflatable central portion 34 lying therebetween.

Extending longitudinally through device 18, between sheets 24, 26, is an end portion of above-mentioned fluid-exchange tube 20. Sheets 24, 26 form a fluid-tight seal about tube 20 at the two locations where the tube intersects margins 32, as shown in FIG. 3 for one of these locations. As seen in this figure, the end regions of the two sheets are sealed about upper and lower semitubular portions of tube 20. Provided within tube 20, where the same is contained within chamber 34, is a plurality of longitudinally-spaced openings, such as openings 30, through which chamber 34 is in fluid communication with the inside of tube 20. The upper end of tube 20 in FIG. 2 is sealed by a plug 38.

Sheets 24, 26 may be constructed from sheet material having suitable strength, elastomeric and fluid-impervious properties, including polyurethane, polyethylene, and polyvinylchloride. As illustrated in FIGS. 3 and 4, sheet 26 has a substantially greater thickness, and hence a lesser degree of flexibility, than sheet 24. Typically, sheet 24 is formed of polyurethane sheet material having a thickness of about 10-mils, and sheet 26 is formed of the same material having a thickness of about 30-mils.

The planar dimensions of sheets 24, 26 are each about 2-inches in width and about 10-inches in length. In nonassembled condition, sheet 26 has a slightly greater width than sheet 24. Device 18 is constructed by placing sheet 24 over sheet 26, with tube 20 positioned therebetween centrally along the longitudinal midline of the two sheets. The side margins of the two sheets are sealed by conventional techniques which may include heat fusion, or a suitable glue or chemical fusing agent. As can be appreciated from FIG. 4, with the side margins of sheets 24, 26 aligned the greater width of sheet 26 exerts an outwardly-directed force at the edges of sheet 24, causing the same to be maintained in a tense, substantially planar condition, which in turn causes sheet 26 to be bowed downwardly as viewed in FIG. 4. Viewing FIG. 5, which shows device 18 positioned within pump 10 in the manner to be described, it is noted that the above-described width difference between sheets 24, 26 permits the device to assume a relaxed, curved transverse cross-section state within the pump.

The above-described structural features of the invention will now be described in relation to the functioning of device 18 in pump 10. Device 18 is positioned in the space between concentric, substantially semi-cylindrical elongate portions of sleeves 12, 14, with the more curved, less flexible sheet 26 contacting the inner wall of sleeve 14, and the less curved, more flexible sheet 24 contacting the outer wall of sleeve 12. As noted above, the different widths of sheets 24, 26 permit device 18 to assume a relaxed position within pump 10 in which the device is generally curved, in transverse cross-section. The parts in device 18 are so dimensioned that the device within pump 10, is in a relaxed state and is held snugly between sleeves 12, 14.

More particularly, as seen cross-sectionally in FIGS. 5 and 6, with pump 10 in operative condition, the outer wall portion of sleeve 12 and the outer sheet of device 18 are adjacent wall 15 of sleeve 14. With particular reference to FIG. 6, it is seen that inner wall portions of sleeve 12 and device 18 confront, and are in contact with, each other. According to an important feature of the present invention, planar margins 32 are disposed between opposed elongate regions of wall 15, and opposed regions of outer wall 12a, also as seen in FIGS. 5 and 6.

In operation, when fluid, e.g. pressurized air, is supplied to chamber 34 through tube 20, this chamber expands, causing inner wall portion 25 of sheet 24 of move from its substantially concave configuration shown in FIG. 5 to its convex configuration shown in FIG. 6, thus producing reciprocal movement of inner wall portion 12b of sleeve 12 from its convex to its concave configuration. Similarly, as fluid is drawn from chamber 34, wall portion 25 is moved from its convex toward its concave configuration, allowing wall portion 12b to move back to its convex configuration, thus to increase the volume of chamber 16. Such reciprocal movement of the inner wall portions of device 18 and sleeve 12, just-described, produce an alternate contraction and expansion of the volume of chamber 16, producing pumping of blood through chamber 16, in a conventional manner. It can be appreciated from the above that as the inner wall members of device 18 and sleeve 12 undergo such reciprocal movement, the noninflatable planar margins of device 18, which are anchored between wall 15 of sleeve 14 and the outer wall portion of sleeve 12, as seen in FIGS. 5 and 6, serves to anchor device 18 against angular and longitudinal movement, within sleeve 14, relative to sleeve 12. Further, because distension of chamber 34 upon inflation of the device occurs primarily through movement of the more flexible sheet 24, the semicylindrical interface between sheet 26 and sleeve 14 remains relatively undistorted during the pumping operation. As a result, the tendency of sheet 26 to shift relative to sleeve 14, as a result of distortion between the two during pumping, is minimized.

Figure 7:
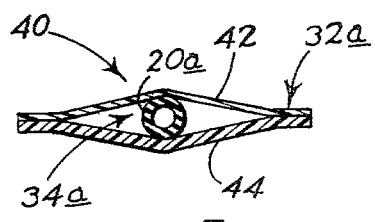
FIG. 7 is a sectional view, similar to FIG. 4, showing an alternate embodiment of the invention.

Referring now to FIG. 7, there is shown in sectional view an alternate embodiment 40 of the present invention. Device 40 is similar in many respects to device 18, and includes a pair of sheets 42, 44 which have substantially the same thicknesses as sheets 24, 26, respectively. Device 40 includes a fluid-exchange tube 20a, planar margins, such as margin 32a, and a chamber 34a. One difference between device 40 and device 18 is that, with the parts in a disassembled condition, the widths of sheets 42, 44 are substantially the same. As a consequence, in the final assembly which is shown in a noninstalled and noninflated condition in FIG. 7, sheets 42, 44 exhibit similar bowing about tube 20a. When placed in use, a device, like device 40, is positioned within a pump, like pump 10, and operates therein substantially in the manner described for device 18. However, an installed device like device 40 conforms to the space between sleeves in such a pump in a slightly less "form-fitting" manner, so to speak, as compared with device 18.

Figure 8:
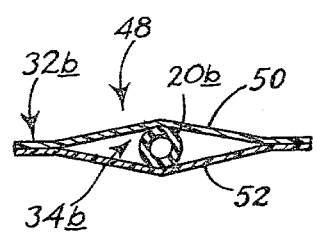
FIG. 8 is a sectional view, similar to FIG. 4, showing a third embodiment of the invention.

Shown sectionally in FIG. 8 is a third embodiment of the invention, indicated at 48. Device 48 is formed of two flexible, fluid-impervious sheets 50, 52. Device 48 also includes a fluid-exchange tube 20b, planar margins, such as margin 32b, and a fluid chamber 34b. Device 48 differs from device 40 in that both sheets forming the device have substantially the same thickness, and hence the same flexibility. Accordingly, the device in a noninstalled condition tends to expand, or distend upon inflation, symmetrically in transverse cross-section. The device further differs from device 18 in that the planar widths of sheets 50, 52 are substantially identical, whereby the transverse cross-section of the device, in its noninstalled, deflated state shown in FIG. 6, is substantially symmetrical. Device 48 functions similarly to devices 18, 40 within a pump, such as pump 10, with its planar margins being sandwiched between sleeves in the pump—thereby preventing migration of the device during pump operation.

A preferred embodiment and several modifications of an inflatable/deflatable device for use in a heart-assist pump have thus been disclosed. Various other modifications and changes may be made without departing from the spirit of the invention, as encompassed in the following claims.

It is claimed and desired to secure by Letters Patent:

1. A body-implantable pump which operates under the influence of a recurrent, cyclic supply and exhaust of external fluid to produce pumping of body fluids, said pump comprising, in operative condition, an elongate envelope having an inner wall which is generally rounded in cross section, a first elongate pumping member having a generally convex, elongate outer wall portion adjacent said inner wall, and an elongate inner wall portion which is movable between generally convex and concave configurations, to increase and decrease the volume of said member, respectively, a second elongate pumping member formed of an outer, elongate, fluid-impermeable sheet adjacent said inner wall, and having opposed elongate side margins, and an inner, elongate, fluid-impermeable sheet having opposed elongate side margins joined with coextending portions of said outer sheets opposed side margins to produce opposed, non-inflatable, fluid-impermeable planar margins disposed between said inner wall and said first member's outer wall portion, and an inner wall portion which confronts said first member's inner wall portion, and which is movable between generally concave and convex configurations to decrease and increase the volume of said second member respectively, wherein said first member's inner wall portion is in its convex and concave configurations, respectively, and conduit means for carrying such external fluid to and from one of said pumping members, thus to produce reciprocal motion in said two members' inner wall portions to pump body fluid in said other pumping member, said non-inflatable planar margins serving to anchor said second wall member to said inner wall and to said first pumping member during such reciprocal motion.

2. Th pump of claim 1 wherein said outer sheet has a greater thickness, and hence less flexibility, than said inner sheet.

3. The pump of claims 1 or 2 wherein said second member is sealed at its opposed ends to provide an inflatable chamber in fluid communication with said conduit means.

* * * * *